(12) United States Patent
Perlman et al.

(10) Patent No.: US 7,501,448 B2
(45) Date of Patent: Mar. 10, 2009

(54) PROCESS FOR PREPARING TELMISARTAN

(75) Inventors: Nurit Perlman, Kfar Saba (IL); Eyal Gilboa, Bat-Yam (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 505 days.

(21) Appl. No.: 11/250,267

(22) Filed: Oct. 13, 2005

(65) Prior Publication Data

US 2006/0094883 A1    May 4, 2006

Related U.S. Application Data

(60) Provisional application No. 60/619,563, filed on Oct. 15, 2004.

(51) Int. Cl.
*A61K 31/4184* (2006.01)
*C07D 235/04* (2006.01)

(52) U.S. Cl. ............... 514/394; 548/301.7; 548/304.7; 548/305.4; 514/385

(58) Field of Classification Search ............ 548/301.7, 548/304.4, 304.7, 305.4; 514/385, 394
See application file for complete search history.

(56) References Cited

U.S. PATENT DOCUMENTS

| 5,591,762 | A  | 1/1997 | Hauel et al. |
| 6,358,986 | B1 | 3/2002 | Schneider et al. |
| 2003/0130331 | A1 | 7/2003 | Donsbach et al. |
| 2003/0139608 | A1 | 7/2003 | Belzer et al. |
| 2004/0110813 | A1 | 6/2004 | Nakatani et al. |
| 2005/0004107 | A1 | 1/2005 | Kohlrausch |

FOREIGN PATENT DOCUMENTS

| CN | 1344712 A | 4/2002 |
| CN | 1412183 A | 4/2003 |
| CN | 1 548 421 | 11/2004 |
| EP | 0253 310 B1 | 10/1994 |
| EP | 0324 377 B1 | 4/1997 |
| EP | 0502 314 B1 | 5/1998 |
| JP | 0629 8684 | 6/1994 |
| WO | WO 00/43370 | 7/2000 |
| WO | WO 00/63158 | 10/2000 |
| WO | WO 03/059327 | 7/2003 |
| WO | WO 2004/028505 | 4/2004 |
| WO | WO 2005/117837 | 12/2005 |
| WO | WO 2006/044648 | 4/2006 |
| WO | WO 2006/044754 A2 | 4/2006 |
| WO | WO 2006/050509 | 5/2006 |

OTHER PUBLICATIONS

Meyers, A.I., et al., The Synthetic Utility of Oxazolines in Aromatic Substitution, Tetrahedron, vol. 41, No. 5, pp. 837-860, 1985.
Ries, Iwe, J., et al., 6-Substituted Benzimidazoles as New Nonpeptide Angiotensin II Receptor Antagonists: Synthesis, Biological Activity, and Structure-Activity Relationships, J. Med. Chem., vol. 36, No. 25, pp. 4040-4051, 1993.
Ansel, et al., *Pharmaceutical Dosage Forms and Drug Delivery Systems*, 7th Ed.
Database Caplus, Chemical Abstracts Service, Columbus Ohio, US; XP002368790 Database accession No. 2005;568830 abstract.
Dinnebier, et al., "Structural Characterization Of Three Crystalline Modifications Of Telmisartan By Single Crystal And High-Resolution X-Ray Power Diffration", *J. Pharm. Sci.*, 2000, pp. 1465-1479, vol. 89, No. 11.
*Perry's Chemical Engineers' Handbook (Sixth Ed.)*, 1984, pp. 20-54 to 20-57.
*Remington: The Science and Practice of Pharmacy*, 19th Ed., vol. II, p. 1627.
International Search Report, for PCT/US2005/037001, mailing date Feb. 24, 2006.

*Primary Examiner*—Golam M Shameem
(74) *Attorney, Agent, or Firm*—Kenyon & Kenyon LLP

(57) ABSTRACT

Provided are processes for preparing telmisartan alkyl ester and telmisartan using environmentally friendly organic solvents that are easily removed from the reaction mixture, wherein a telmisartan alkyl ester is isolated and hydrolyzed to form telmisartan or the telmisartan is prepared using a synthesis in a single reaction vessel.

1 Claim, No Drawings

PROCESS FOR PREPARING TELMISARTAN

RELATED APPLICATIONS

The present application claims the benefit of U.S. Provisional Patent Application No. 60/619,563 filed on Oct. 15, 2004.

FIELD OF THE INVENTION

The present invention is directed to processes for preparing a telmisartan alkylester intermediate and further converting it to telmisartan. The present invention is also directed to a process for the preparation of telmisartan in a single vessel.

BACKGROUND OF THE INVENTION

Telmisartan, 4'-[2-n-propyl-4-methyl-6-(1-methylbenzimid-azol-2-yl)benzimidazol-1-ylmethyl]biphenyl-2-carboxylic acid, having the structure of formula I

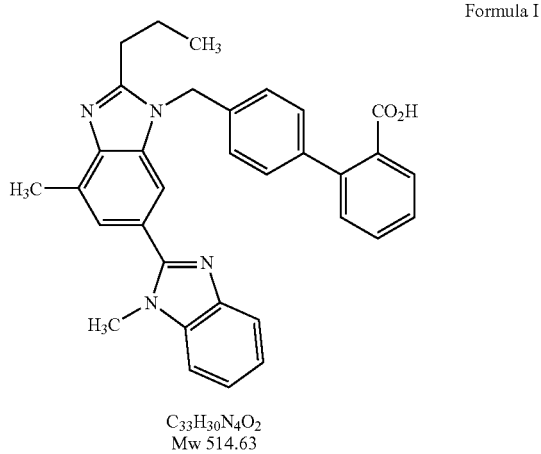

Formula I $C_{33}H_{30}N_4O_2$
Mw 514.63 is a non-peptide angiotensin II receptor (type $AT_1$) antagonist. The United States Food and Drug Administration (FDA) approved it for the treatment of hypertension. It may be used alone or in combination with other hypertensive agents, such as hydrochlorothiazide. Boehringer Ingelheim markets telmisartan under the trade name Micardis® (telmisartan), available as 40 and 80 mg tablets for oral administration. Two patents are listed in the FDA's electronic Orange Book for telmisartan, U.S. Pat. No. 6,358,986 ("the '986 patent") and U.S. Pat. No. 5,591,762 ("the '762 patent").

The '986 patent discloses that telmisartan and the physiologically acceptable salts thereof can also be used to treat cardiac insufficiency, ischaemic peripheral circulatory disorders, myocardial ischaemia (angina), diabetic neuropathy, glaucoma, gastrointestinal diseases, bladder diseases, and to prevent progression of cardiac insufficiency after myocardial infarct.

In addition to the above therapeutic applications of telmisartan, the '762 patent discloses other therapeutic applications, including treating diabetic nephropathy, pulmonary diseases, e.g., lung oedema and chronic bronchitis. It also discloses using telmisartan to prevent arterial restenosis after angioplasty, thickening of blood vessel walls after vascular operations, and diabetic angiopathy. The '762 patent further discloses using telmisartan to alleviate central nervous system disorders, such as depression, Alzheimer's disease, Parkinson Syndrome, bulimia, and disorders of cognitive function in view of the effects of angiotensin on the release of acetylchloline and dopamine in the brain.

The European Application No. EP 0502314 and its corresponding U.S. patent, the '762 patent disclose preparing telmisartan by alkylation of 1,7'-dimethyl-2'-propyl-1H, 3'H-[2,5'] bibenzoimidazolyl (referred to as BIM) with a 4'-[(bromomethyl)[1,1'-biphenyl]-2-carboxylic acid 1,1-dimethylethyl ester (referred to as a BMBP alkyl ester) followed by hydrolysis.

Chinese patent application, CN 1344712A, filed July 2001 discloses a process to prepare telmisartan by reacting 1,7'-dimethyl-2'-propyl-1H, 3'H-[2,5']bibenzoimidazolyl with 4'-bromomethyl-biphenyl-2-carboxylic acid methyl or ethyl ester to form a telmisartan methyl or ethyl ester intermediate, which is converted to telmisartan by acid or base hydrolysis.

BIM may be prepared by mixing 2-propyl-4-methyl-1H-benzimidazole-6-carboxylic acid with N-methyl-o-phenylene-diamine dihydrochloride as disclosed in J. Med. Chem. (1993), 36(25), 4040-51, International Patent Application WO 0063158, and US Application No. 2003/0139608 and are hereby incorporated by reference for their disclosure of processes for preparing BIM. US Application No. 2003/0139608 discloses a process, which can be used on an industrial scale for preparing and purifying BIM, in which the crude product is subjected to charcoal treatment.

The BMBP alkylester, wherein the alkyl group is a $C_{1-4}$ branched or straight chain may be prepared as disclosed in EP Patent No. 253,310, Meyers et al., Tetrahedron 1985 vol. 41, 837-860, European Patent No 324,377, and Japanese Patent No. 06298684. Each of these references is hereby incorporated by reference for their disclosure of processes for preparing a BMBP alkylester.

The solvents previously used to prepare telmisartan, such as dimethylformamide and dimethylsulfoxide, have a high boiling point of greater than about 150° C. These solvents are difficult to remove from the reaction using various evaporation techniques known in the art. These reaction conditions are less environmentally friendly, less efficient, and harsher on the product, and therefore result in a lower yield of the telmisartan alkylester intermediate product. Other previously used solvents to prepare telmisartan are miscible with water and therefore cause difficulties in extracting the organic telmisartan alkylester intermediate products from the reaction. Other solvents are toxic or unsafe for other reasons. Also, processes previously disclosed use 1.5 equivalents of BIM for each equivalent of a BMBP alkyl ester, which is in excess of what is theoretically required. The expense of the reagents in the preparation and isolation of BIM results in a more expensive overall synthesis of telmisartan than should theoretically be required.

Thus, there is a need for processes for the preparation of telmisartan alkylester and telmisartan that are environmentally friendly, easy to practice, produce high yields of telmisartan, less costly and that can be adapted to industrial scale.

SUMMARY OF THE INVENTION

In one aspect, the present invention provides a process for preparing a telmisartan alkylester intermediate of formula II

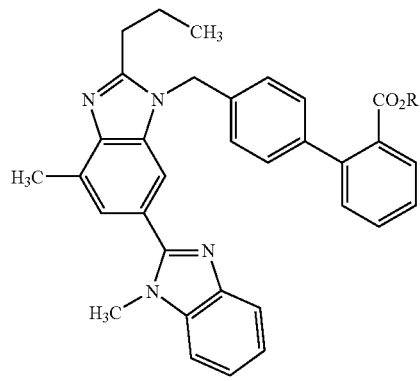

Formula II comprising the steps of
(a) combining 1,7'-dimethyl-2'-propyl-1H,3'H-[2,5']bibenzoimidazolyl (referred to as BIM) of formula III,

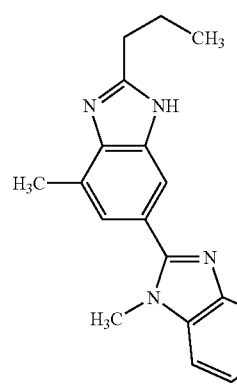

Formula III with a 4'bromomethyl-biphenyl-2-carboxylic acid alkyl ester (referred to as BMBP alkyl ester) of formula IV

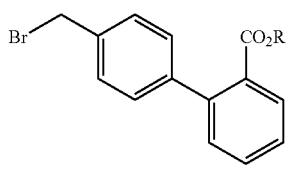

Formula IV an inorganic base and a low boiling point organic solvent to obtain a mixture;
(b) heating the mixture obtained in step (a) to a temperature of about 55° C. to about 120° C.;
(c) maintaining the mixture obtained in step (b) for about 1 hour to about 8 hours to obtain a telmisartan alkylester of formula II; and
(d) recovering the telmisartan alkylester of formula II; wherein,
R is a straight or branched chain $C_1$-$C_4$ alkyl.

In another aspect, the present invention provides a process for preparing telmisartan by converting a telmisartan alkylester intermediate of formula II described above to telmisartan of formula I, preferably by a process of hydrolysis under acidic or basic conditions.

In yet another aspect, the present invention provides a process for the preparation of telmisartan of formula I

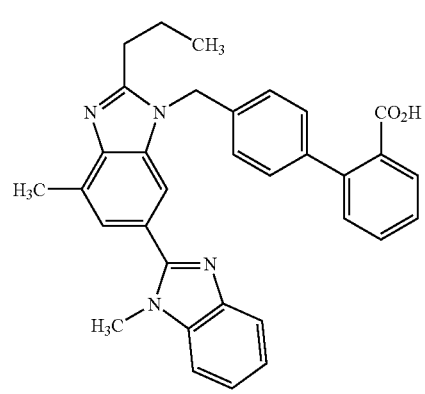

Formula I in a single reaction vessel comprising the steps of
(a) combining BIM of formula III, a BMBP alkyl ester of formula IV, an inorganic base and a ketone solvent, to obtain a mixture;
(b) heating the mixture obtained in step (a) to a temperature of about 55° C. to about 120° C.;
(c) maintaining the mixture obtained in step (b) for about 6 hours to about 24 hours to obtain a telmisartan salt of formula V;

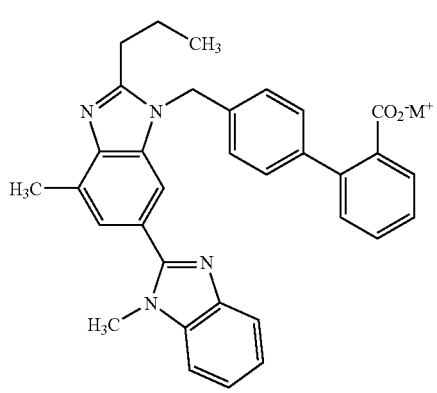

Formula V (d) separating the organic phase containing a telmisartan salt of formula V from the aqueous phase;
(e) converting telmisartan salt of formula V to telmisartan of formula I; and
(f) recovering telmisartan of formula I,
wherein,
R is a straight or branched chain $C_1$-$C_4$ alkyl, and
M is a metal atom.

In one aspect the invention provides pharmaceutical compositions comprising telmisartan prepared according to the processes of the present invention and pharmaceutically acceptable excipients.

In another aspect the present invention provides a process for preparing pharmaceutical formulation comprising mixing telmisartan prepared according to processes of the present invention, and a pharmaceutically acceptable carrier.

DETAILED DESCRIPTION OF THE INVENTION

As used herein, the term "low boiling temperature" refers to a boiling temperature between about 55° C. to about 120° C.

As used herein, the term "PTC (phase transfer catalyst)" refers to an agent, which is used in a small amount in a two phase reaction, for extracting the reactant from one phase to the other. Typical PTCs are for example, crown ethers and quaternary ammonium salts.

As used herein, the term "base" refers to a substance that tends to accept a proton. Typical bases are for example, alkaline hydroxide and amines. Hence, an inorganic base is a substance, which contains a metal cation and does not contain an organic moiety, as compared to an organic base, which is a substance that contains an organic moiety. Typical inorganic bases are for example, metal hydroxide, such as sodium hydroxide and potassium hydroxide, metal carbonates, such as sodium carbonate and potassium bicarbonate.

As used herein, the term "acid" refers to a substance that tends to release a proton. Typical acids are for example, mineral acids, such as HCl and organic acids, such as trifluoroacetic acid and acetic acid. Hence, a weak acid refers to a substance that tends to a partial dissociation in water. Typical weak acids are for example, acetic acid, para-toluenesulfonic acid and $H_2CO_3$.

The present invention provides a process for preparing a telmisartan alkylester intermediate of formula II

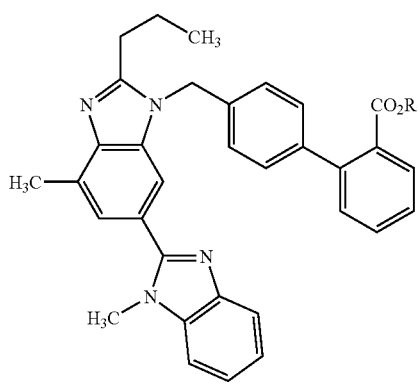

Formula II comprising the steps of
(a) combining 1,7'-dimethyl-2'-propyl-1H,3'H-[2,5']bibenzoimidazolyl (referred to as BIM) of formula III,

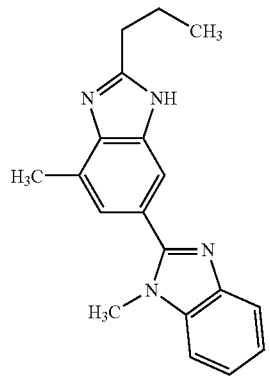

Formula III with a 4'bromomethyl-biphenyl-2-carboxylic acid alkyl ester (referred to as BMBP alkyl ester) of formula IV,

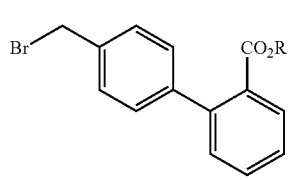

Formula IV an inorganic base, and an a low boiling point organic solvent, to obtain a mixture;

(b) heating the mixture obtained in step (a) to a temperature of about 55° C. to about 120° C.;

(c) maintaining the mixture obtained in step (b) for about 1 hour to about 8 hours, to obtain a telmisartan alkylester of formula II, and (d) recovering a telmisartan alkylester of formula II, wherein, R is a straight or branched chain $C_1$-$C_4$ alkyl.

Preferably, the straight or branched chain $C_1$-$C_4$ alkyl is methyl.

The solvents used in the process of the present invention have a boiling temperature less than about 120° C. Thus, these solvents are easy to remove from the reaction using various evaporation techniques known in the art. Therefore, a lower reaction temperature is applied. Moreover, almost all of the solvents used in the present invention to prepare telmisartan are slightly to non-miscible with water and therefore do not cause difficulties in extracting the organic telmisartan alkylester intermediate products from the reaction. Also, these solvents are non-toxic, safe and environmentally friendly.

Preferably, the low boiling point solvent is selected from the group consisting of $C_{6-10}$ aromatic hydrocarbon, ketone and ester and mixtures thereof. Preferably, the $C_{6-10}$ aromatic hydrocarbon is toluene. Preferably, the ketone is methylethylketone, methylisobutylketone or acetone. A preferred ester is isobutylacetate. The more preferred solvent is toluene.

Preferably, water can be added to the low boiling point organic solvent in step (a).

The process of the present invention uses about 0.9 to about 1 mole equivalents of BIM per mole equivalent of a BMBP alkyl ester. Thus, allowing a facile separation of the product from BIM and therefore, leading to a significantly less expensive and time consuming process.

Preferably, the amount of BIM used in step (a) is of about 0.8 to about 1.5 mole equivalents per mole equivalent of BMBP, more preferably, of about 0.9 to about 1 mole equivalents per mole equivalent of BMBP.

The process of the present invention uses an inorganic base instead of an organic base. Therefore, disposing of the base in the work-up stages is very simple and more environmental friendly. Preferably, the inorganic base is selected from the group consisting of a metal hydroxide and a metal carbonate. Preferably, the metal hydroxide is sodium hydroxide, potassium hydroxide, cesium hydroxide, barium hydroxide, magnesium hydroxide, calcium hydroxide or strontium hydroxide. Preferably, the metal carbonate is sodium carbonate, sodium bicarbonate, potassium carbonate, potassium bicarbonate or cesium carbonate. Preferably the inorganic base is either potassium carbonate or sodium hydroxide.

Preferably, an aqueous solution of an inorganic base is used in step (a). Optionally, water can be added to step (a) when a solid inorganic base is used.

When a two-phase system is formed, such as for example, when the solvent is toluene, the reaction may occur at the interface between the two phases. Hence, the rate of such an interfacial reaction may be greatly increased by use of a phase transfer catalyst (PTC). Preferably, the PTC is selected from the group consisting of quaternary ammonium compounds, crown ether and phosphonium compounds. A preferred quaternary ammonium compound includes, tributylmethylammonium chloride (Aliquat® 175), tetrabutylammionium bromide (TBAB), tetrabutylammonium hydrogensulphate (TBAHS), benzyltriethylammonium chloride and tetrapropylammonium bromide (TPAB).

Preferably, the temperature of step (b) is of about 78° C. to about 110° C.

Telmisartan alkylester of formula II may be recovered by any method known in the art, such as the steps of cooling the reaction mixture of step (c), filtering, washing the organic phase with water and drying the organic phase, filtering and evaporating the solvent.

The present invention also provides a process for preparing telmisartan by converting telmisartan alkylester intermediate of formula II described above to telmisartan of formula I, preferably according to the hydrolysis process under acidic conditions as disclosed in U.S. Pat. No. 5,591,762 or under basic conditions, as disclosed in CN patent application NO. 1344712A.

Hydrolysis of a telmisartan alkylester of formula II to give telmisartan may be conducted under acidic conditions or under basic conditions, as described above.

The process of the present invention can be done in a single vessel, by obtaining the salt of telmisartan after hydrolysis of telmisartan alkylester. Because of the high concentration of salts in the aqueous phase, the phases separate spontaneously and the telmisartan salt, which is located in the organic phase, is then isolated by adding an acid to the reaction vessel.

The present invention further provides a process for the preparation of telmisartan of formula I

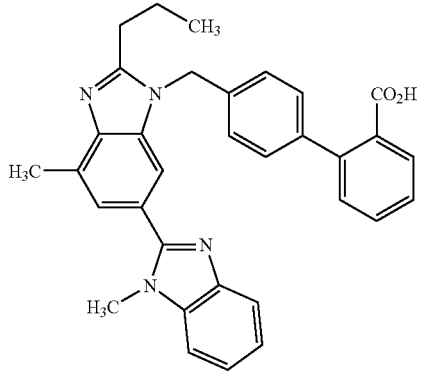

Formula I in a single reaction vessel comprising the steps of
(a) combining BIM of formula III, a BMBP alkylester of formula IV, an inorganic base and a ketone solvent, to obtain a mixture;
(b) heating the mixture obtained in step (a) to a temperature of about 55° C. to about 120° C.;
(c) maintaining the mixture obtained in step (b) for 6 hours to about 24 hours, to obtain telmisartan salt of formula V;

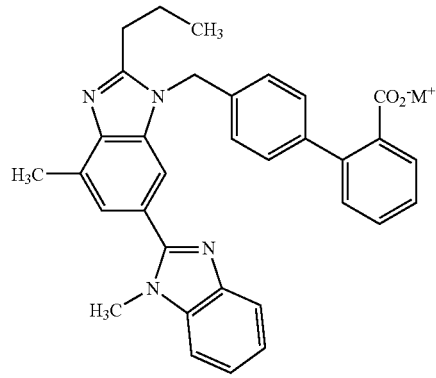

Formula V (d) separating the organic phase containing telmisartan salt of formula V, from the aqueous phase;
(e) converting telmisartan salt of formula V to telmisartan of formula I; and
(f) recovering telmisartan of formula I,
wherein,
R is a straight or branched chain $C_1$-$C_4$ alkyl;
M is a metal atom.

Preferably, the straight or branched chain $C_1$-$C_4$ alkyl is methyl.

Preferably, the metal atom is derived from the inorganic base.

The inorganic bases, BIM and their amounts are the same as those described in the process for the preparation of telmisartan alkylester of formula II.

Preferably, the ketone is methylethylketone, methylisobutylketone or acetone. The more preferred solvent is acetone.

Preferably, water can be added to the ketone solvent in step (a).

The temperature of step (b) is the same as the temperature described in the process for the preparation of a telmisartan alkylester of formula II.

Preferably, a telmisartan salt may be converted to telmisartan by adding an acid to the organic phase obtained in step (d), containing a telmisartan salt of formula V, preferably to obtain a pH of less than about 6, more preferably, of about 4 to about 6. Preferably, the acid used is trifluoroacetic acid, sulfuric acid, or acetic acid. The more preferred acid is acetic acid.

Telmisartan may be recovered by any method known in the art, such as filtering and drying.

To conclude, the reaction conditions applied in the processes of the present invention are more environmentally friendly, more efficient, and mild on the product, leading to a much higher yield of the telmisartan alkylester intermediate product and thus, can be adapted to an industrial scale.

The present invention provides pharmaceutical compositions comprising telmisartan prepared according to the processes of the present invention and pharmaceutically acceptable excipient.

The present invention further provides a process for preparing pharmaceutical formulation comprising mixing telmisartan prepared according to processes of the present invention, and a pharmaceutically acceptable carrier.

As used herein, the term "pharmaceutical compositions" includes tablets, pills, powders, liquids, suspensions, emulsions, granules, capsules, suppositories, or injection preparations. Pharmaceutical compositions containing the telmisartan of the present invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Any excipient commonly known and used widely in the art can be used in the pharmaceutical composition. Carriers used include, but are not limited to, lactose, white sugar, sodium chloride, glucose, urea, starch, calcium carbonate, kaolin, crystalline cellulose, silicic acid, and the like. Binders used include, but are not limited to, water, ethanol, propanol, simple syrup, glucose solutions, starch solutions, gelatin solutions, carboxymethyl cellulose, shelac, methyl cellulose, potassium phosphate, polyvinylpyrrolidone, and the like. Disintegrating agents used include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, and the like. Disintegration inhibitors used include, but are not limited to, white sugar, stearin, coconut butter, hydrogenated oils, and the like. Absorption accelerators used include, but are not limited to, quaternary ammonium base, sodium laurylsulfate, and the like. Wetting agents used include, but are not limited to, glycerin, starch, and the like. Adsorbing agents used include, but are not limited to, starch, lactose, kaolin, bentonite, colloidal silicic acid, and the like. Lubricants used include, but are not limited to, purified talc, stearates, boric acid powder, polyethylene glycol, and the like. Tablets can be further coated with commonly known coating materials such as sugar coated tablets, gelatin film coated tablets, tablets coated with enteric coatings, tablets coated with films, double layered tablets, and multi-layered tablets.

When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like.

For the purpose of shaping the pharmaceutical composition in the form of suppositories, any commonly known excipient used in the art can be used. For example, excipients include, but are not limited to, polyethylene glycols, coconut butter, higher alcohols, and esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic.

Additional ingredients, such as dissolving agents, buffer agents, and analgesic agents may be added. If necessary, coloring agents, preservatives, perfumes, seasoning agents, sweetening agents, and other medicines may also be added to the desired preparations.

The amount of telmisartan or salt thereof contained in a pharmaceutical composition for treating schizophrenia should be sufficient to treat, ameliorate, or reduce the symptoms associated with schizophrenia. Preferably, telmisartan is present in an amount of about 1% to about 70% by weight, and more preferably from about 1% to about 30% by weight of the dose.

The pharmaceutical compositions of the invention may be administered in a variety of methods depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations may be administered intramuscularly, intracutaneously, subcutaneously or intraperitoneally. Suppositories may be administered into the rectum.

The dosage of a pharmaceutical composition for treating schizophrenia according to the invention will depend on the method of use, the age, sex, and condition of the patient. Preferably, telmisartan is administered in an amount from about 0.1 mg/kg to about 10 mg/kg of body weight/day. More preferably, about 1 mg to 200 mg of telmisartan may be contained in a dose.

The invention also encompasses methods of making a pharmaceutical formulation comprising combining telmisartan, and a pharmaceutically acceptable excipient. As used herein, the term "pharmaceutical formulations" includes tablets, pills, powders, liquids, suspensions, solutions, emulsions, granules, capsules, suppositories, or injection preparations.

Having described the invention with reference to certain preferred embodiments, other embodiments will become apparent to one skilled in the art from consideration of the specification. The invention is further defined by reference to the following examples describing in detail the preparation of the compound of the present invention. It will be apparent to those skilled in the art that many modifications, both to materials and methods, may be practiced without departing from the scope of the invention.

EXAMPLES

Example 1

Preparation of Telmisartan Alkylester of Formula II 1,7'-dimethyl-2'-propyl-1H,3'H-[2,5']bibenzoimidazolyl (BIM) (4 g), Aliquat® 175 (1.36 ml), $K_2CO_3$ (8.19 g), and toluene (50 ml) were added to a 250 ml round bottom flask equipped with a magnetic stirring bar and reflux condenser. The mixture was heated to reflux (about 85-90° C.) until a clear brown organic solution was obtained. 4'bromomethyl-biphenyl-2-carboxylic acid (BMBP) methyl ester (4.5 g) in toluene (24 ml) was added to the clear brown organic solution to form a reaction mixture. The reaction mixture was stirred for about 6 hrs then cooled by ice bath and filtered forming a cooled reaction mixture. The cooled reaction mixture was then extracted twice with water (20 ml), dried over $MgSO_4$, and evaporated forming telmisartan methyl ester (5.02 g), which is about a 69% yield.

Example 2

Preparation of Telmisartan Alkylester of Formula II 1,7'-dimethyl-2'-propyl-1H,3'H-[2,5']bibenzoimidazolyl (BIM) (4 g), NaOH (4.26 g in 15 ml of water), and methylethylketone (40 ml) were added to a 250 ml round bottom flask equipped with a magnetic stirring bar and reflux condenser forming a mixture. The mixture was heated to reflux until a clear BIM solution was obtained. A solution of 4'bromomethyl-biphenyl-2-carboxylic acid (BMBP) methyl ester (4.5 g) in methylethylketone (16 ml) was added to the clear BIM solution forming a reaction mixture. The reaction mixture was stirred for about 2 hrs then cooled to room temperature. The cooled reaction mixture was then extracted with water (15 ml), dried over $MgSO_4$, and evaporated to obtain telmisartan methylester (5.76 g), which is about a 79% yield.

Example 3

Preparation of Telmisartan Alkylester of Formula II 1,7'-dimethyl-2'-propyl-1H,3'H-[2,5']bibenzoimidazolyl (BIM) (4 g), tetrabutylammonium hydrogensulphate (TBAHS) (0.45 g) and NaOH (1.05 g), water (15 ml), and toluene (40 ml) were added to a 250 ml round bottom flask equipped with a magnetic stirring bar and reflux condenser forming a BIM mixture. The BIM mixture was heated at reflux (80-90° C.). A solution of 4'bromomethyl-biphenyl-2-carboxylic acid (BMBP) methyl ester (4.5 g) in toluene (16 ml) was added to the warm BIM mixture forming a reaction mixture and the reaction mixture was stirred for 3.5 hrs then cooled to room temperature. The cooled reaction mixture was then extracted with water (15 ml forming an aqueous phase and organic phase. The organic phase was dried over $MgSO_4$ then evaporated to obtain telmisartan methylester (7.41 g), which is about a 100% yield.

Example 4

Preparation of Telmisartan Alkylester of Formula II 1,7'-dimethyl-2'-propyl-1H,3'H-[2,5']bibenzoimidazolyl (BIM) (4 g), Aliquat® 175 (0.47 ml), NaOH (4.85 g), water (16 ml), and isobutylacetate (40 ml) were added to a 250 ml round bottom flask equipped with a magnetic stirring bar and reflux condenser and heated at reflux (80° C.) forming a warm BIM mixture. 4'bromomethyl-biphenyl-2-carboxylic acid (BMBP) methyl ester (4.5 g) in isobutylacetate (16 ml) was added to the warm BIM mixture to form a reaction mixture and the reaction mixture was stirred for about one hour then cooled to room temperature. The cooled reaction mixture was then extracted with water (20 ml) forming an aqueous phase and organic phase. The organic phase was dried over $MgSO_4$ then evaporated to obtain telmisartan methylester (5.56 g), which is about a 76% yield.

Example 5

Preparation of Telmisartan

A 250-ml round bottom flask was loaded with BIM (4 g), methylethylketone (40 ml), and aqueous NaOH (22% or 19.26 grams) to form a BIM mixture. The BIM mixture was heated to 80° C. and a solution of BMBP methylester (4 g.) in methylethylketone (16 ml) was added to the BIM mixture forming a reaction mixture. The reaction mixture was stirred for about 24 hrs forming an organic phase and an aqueous phase. The two phases were separated and the organic phase was divided into two portions. About 1 ml of glacial acetic acid was added to one of the two portions until the pH was adjusted to about 4.7 forming a solution with a precipitate after a few minutes. The solution was stirred at room temperature over night forming a product. The product was isolated by vacuum filtration and dried in a vacuum oven at 50° C. for 24 hr to obtain 2.7 g or 80% yield of Telmisartan.

The second portion was evaporated forming a solid. The solid was dissolved in absolute ethanol, or in methanol heated to reflux, and glacial acetic acid was added, adjusting the pH to 5.5 forming an ethanol solution. After 40 minutes the ethanol solution was cooled to room temperature and stirred for 24-hrs forming telmisartan precipitate. The telmisartan precipitate was isolated by vacuum filtration, washed with ethanol and dried in a vacuum oven at 50° C. for 24 hr.

Example 6

Preparation of Telmisartan

A 250-ml round bottom flask was loaded with BIM (8 g), Acetone (96 ml) and an aqueous NaOH solution (35%, 20 ml) to form a BIM mixture, which was heated, at reflux. BMBP methylester (8 g) in acetone (32 ml) was added to the warm BIM mixture forming a reaction mixture. The reaction mixture was stirred at reflux for 24 hrs forming an organic phase and an aqueous phase. The phases were separated and the organic phase was divided into two portions. The first organic portion (48-ml) was heated to reflux and glacial acetic acid (1 ml) was added, adjusting the pH to 5.5. The first organic portion was then cooled to room temperature and stirred over night forming a precipitate. The precipitate was isolated by vacuum filtration, washed with acetone (40 ml), and dried in a vacuum oven at 50° C. for 24 hrs to obtain 6.58 g of telmisartan (79% yield).

The second portion (48-ml) was evaporated forming a solid. The solid was dissolved in absolute ethanol, or in methanol heated to reflux, and glacial acetic acid (about 1 ml) was added, adjusting the pH to 5.5 forming an ethanol solution. After 40 minutes the ethanol solution was cooled to room temperature and stirred 24-hrs forming telmisartan precipitate. The telmisartan precipitate was isolated by vacuum filtration, washed with ethanol, (40 ml) and dried in a vacuum oven at 50° C. for 24 hrs to obtain 4.92 g of telmisartan (71% yield).

Example 7

Preparation of Telmisartan

A 100 ml reactor was loaded with BIM (4 g), methylisobutylketone (48 ml) and an aqueous NaOH solution (35%, 10 ml) forming a BIM mixture. The BIM mixture was heated to 78° C. and a solution of BMBP methylester (4 g) in methylisobutylketone (16 ml) was added to the warmed BIM mixture forming a reaction mixture. The reaction mixture was stirred at reflux for 24 hrs forming a reaction mixture with an organic phase and an aqueous phase. The phases were separated and glacial acetic acid (2 ml) was added to the organic phase. After 2 hrs the reaction mixture was cooled to room temperature and stirred 3 hrs forming a telmisartan precipitate. The telmisartan precipitate was isolated by vacuum filtration, washed with ethanol (40 ml), and dried in a vacuum oven at 50° C. for 24 hrs to obtain 4.59 g of telmisartan (68% yield).

What is claimed is:

1. A process for preparing telmisartan of formula I:

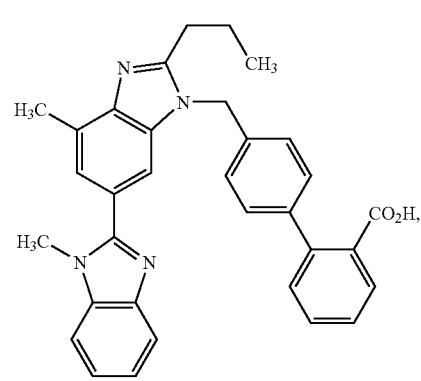

Formula I said process comprising the steps of
(a) combining 1,7'-dimethyl-2'-propyl-1H-3'H-[2.5'] bibenzoimidazolyl of formula III:

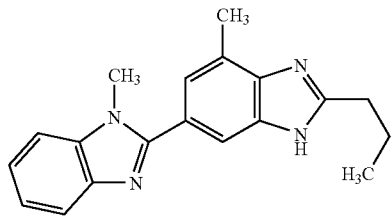

Formula III with a 4'-bromomethyl-biphenyl-2-carboxylic acid alkyl ester of formula IV:

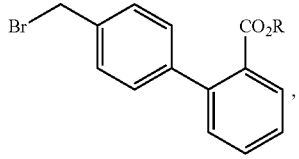

Formula IV an inorganic base and a low boiling point organic solvent, to obtain a mixture;

(b) heating the mixture obtained in step (a) to a temperature of about 55° C. to about 120° C.;
(c) maintaining the mixture obtained in step (b) for about 1 hour to about 8 hours, to obtain telmisartan alkylester of formula II:

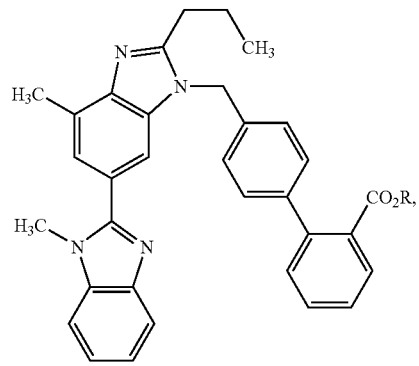

Formula II wherein R is a straight or branched chain $C_1$-$C_4$ alkyl;
(d) recovering the telmisartan alkylester of formula II; and
(e) hydrolyzing the telmisartan alkylester of formula II under acidic or basic conditions to obtain telmisartan of formula I.

* * * * *